(12) United States Patent
Horn (10) Patent No.: US 10,317,344 B2
(45) Date of Patent: Jun. 11, 2019

(54) SPEED ENHANCEMENT OF CHROMATIC CONFOCAL METROLOGY

(71) Applicant: KLA-Tencor Corporation, Milpitas, CA (US)

(72) Inventor: Paul Horn, Milpitas, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 15/690,969

(22) Filed: Aug. 30, 2017

(65) Prior Publication Data

US 2018/0067058 A1 Mar. 8, 2018

Related U.S. Application Data

(60) Provisional application No. 62/384,324, filed on Sep. 7, 2016.

(51) Int. Cl.
*G01N 21/00* (2006.01)
*G01N 21/88* (2006.01)
*G01B 11/06* (2006.01)
*G01N 21/95* (2006.01)
*G01N 21/956* (2006.01)

(52) U.S. Cl.
CPC ..... *G01N 21/8806* (2013.01); *G01B 11/0608* (2013.01); *G01N 21/9501* (2013.01); *G01N 21/95684* (2013.01); *G01N 2201/068* (2013.01); *G01N 2201/0638* (2013.01); *G01N 2201/06113* (2013.01); *G01N 2201/08* (2013.01); *G01N 2201/10* (2013.01)

(58) Field of Classification Search
None
See application file for complete search history.

(56) References Cited

U.S. PATENT DOCUMENTS 4,689,491 A * 8/1987 Lindow ................ G01N 21/956
250/559.07
4,844,617 A * 7/1989 Kelderman .............. G01B 9/04
356/624

(Continued)

FOREIGN PATENT DOCUMENTS

FR 2950441 † 3/2011
JP 2002296018 A * 2/2002

(Continued)

OTHER PUBLICATIONS

ISA/KR, International Search Report for PCT/US2017/050326 dated Dec. 19, 2017.

(Continued)

*Primary Examiner* — Dominic J Bologna
(74) *Attorney, Agent, or Firm* — Hodgson Russ LLP (57) ABSTRACT

Systems and methods for height measurements, such as those for bumps, pillars, or film thickness, can use chromatic confocal techniques. The system can include a white light source that emits white light and lenses that vary a focal distance of each wavelength of the white light from the white light source. Each of the wavelengths of the white light focuses at a different distance from the lenses. A sensor body has multiple sensors that are disposed in the sensor body in multiple rows and columns. Each of the rows and the columns has at least two of the sensors.

13 Claims, 5 Drawing Sheets

(56) References Cited

U.S. PATENT DOCUMENTS

| | | | | |
|---|---|---|---|---|
| 6,248,988 B1* | 6/2001 | Krantz | ............... | G02B 21/004 250/201.3 |
| 6,552,803 B1 | 4/2003 | Wang et al. | | |
| 6,636,310 B1* | 10/2003 | Ben-Dov | ............... | G01B 11/24 356/601 |
| 6,838,650 B1* | 1/2005 | Toh | ............... | G02B 21/0024 250/201.3 |
| 6,858,859 B2 | 2/2005 | Kusunose | | |
| 6,917,421 B1 | 7/2005 | Wihl et al. | | |
| 7,633,616 B2 | 12/2009 | Hing | | |
| 8,194,301 B2* | 6/2012 | Zhao | ............... | G01N 21/8806 359/204.1 |
| 9,739,600 B1* | 8/2017 | Fresquet | ............... | G01B 11/22 |
| 2005/0030528 A1* | 2/2005 | Geffen | ............... | G01B 11/026 356/237.1 |
| 2008/0031509 A1 | 2/2008 | Heiden et al. | | |
| 2008/0130013 A1* | 6/2008 | Stautmeister | ......... | G01B 11/24 356/609 |
| 2008/0186472 A1* | 8/2008 | Park | ............... | G01J 5/0003 356/51 |
| 2011/0235045 A1* | 9/2011 | Koerner | ............. | G02B 21/0056 356/451 |
| 2012/0019821 A1* | 1/2012 | Chen | ............... | G02B 21/0032 356/303 |
| 2012/0156636 A1† | 6/2012 | Stock | | |
| 2013/0063721 A1* | 3/2013 | Fujii | ............... | G01J 3/2803 356/306 |

FOREIGN PATENT DOCUMENTS

| | | |
|---|---|---|
| JP | 2002296018 A | 10/2002 |
| WO | 03036227 A1 | 5/2003 |

OTHER PUBLICATIONS

Press release New CHRocodile MPS 2L Sensor for Inline-Inspection of Container Glass at the Cold End, 1 page, published on Sep. 5, 2016 on website www.precitec.de.†

\* cited by examiner
† cited by third party

SPEED ENHANCEMENT OF CHROMATIC CONFOCAL METROLOGY

CROSS-REFERENCE TO RELATED APPLICATIONS

This application claims priority to the provisional patent application filed Sep. 7, 2016 and assigned U.S. App. No. 62/384,324, the disclosure of which is hereby incorporated by reference.

FIELD OF THE DISCLOSURE

This disclosure relates to optical sensors.

BACKGROUND OF THE DISCLOSURE

Evolution of the semiconductor manufacturing industry is placing ever greater demands on yield management and, in particular, on metrology and inspection systems. Critical dimensions are shrinking while wafer size is increasing. Economics is driving the industry to decrease the time for achieving high-yield, high-value production. Thus, minimizing the total time from detecting a yield problem to fixing it determines the return-on-investment for the semiconductor manufacturer.

Fabricating semiconductor devices, such as logic and memory devices, typically includes processing a semiconductor wafer using a large number of semiconductor fabrication processes to form various features and multiple levels of the semiconductor devices. For example, lithography is a semiconductor fabrication process that involves transferring a pattern from a reticle to a photoresist arranged on a semiconductor wafer. Additional examples of semiconductor fabrication processes include, but are not limited to, chemical-mechanical polishing (CMP), etch, deposition, and ion implantation. Multiple semiconductor devices may be fabricated in an arrangement on a single semiconductor wafer and then separated into individual semiconductor devices.

Prior to being separated into individual semiconductor devices, an entire wafer of semiconductor devices may be prepared for packaging. Packaging may include coupling a chip carrier such as a substrate to a semiconductor device. Preparing a wafer of semiconductor devices for packaging may include forming structures on a surface of the semiconductor devices that may be used to couple a semiconductor device to a chip carrier. For example, relatively small solder balls may be arranged in an area on a semiconductor device. Such relatively small solder balls may be commonly referred to as "bumps," and a wafer on which such solder balls are formed may be commonly referred to as a "bumped wafer." The bumps may be, for example, half sphere or rectangular. The bumps may be configured to physically attach the semiconductor device to a chip carrier and to make electrical connection to a chip carrier. For example, a device may be placed on a substrate, and the solder balls may contact and melt onto an array of metal pads on the substrate. Such a packaging method may be commonly referred to as face-down bonding, flip-chip bonding, or controlled collapse chip connections ("C4").

A chip can contain a large number of bumps. The bumps should be the same height to connect them to the board at the same time. However, bumps generally vary in height due to differences in the manufacturing process.

Bumps that are incorrectly formed on a wafer, such as those outside a height tolerance, may cause significant problems during processing, such as probing of the wafer and during use of the device. For example, incorrectly formed bumps may damage probes on a probe card thereby causing tester downtime and incurring tester repair costs. Incorrectly formed bumps may also bridge power and ground contacts thereby resulting in excessive current draw through a probe card. Therefore, bumped wafers may typically be inspected and measured prior to probing. In addition, incorrectly formed bumps may not be detected during probing and may increase the potential for failure of a packaged device. Furthermore, probing may damage bumps especially on a wafer having a relatively high number of bumps per unit area that may require high vertical forces during testing to seat probes for proper contact. In this manner, inspection and metrology of a bumped wafer may also be performed after wafer probing.

Currently available methods for three-dimensional inspection and metrology of bumped wafers generally include first acquiring data in the x-y plane and then acquiring data in the z plane. Essentially, such systems may be described as being serial in data acquisition (i.e., two-dimensional ("2D") data acquisition followed by three-dimensional ("3D") data acquisition). For bumped wafers, 2D defects may include, for example, missing bumps, improperly located bumps, bridged bumps, large-diameter bumps, and small-diameter bumps. Examples of 3D defects may include, but are not limited to, bumps that may be too tall or too short or that may have protruding vertical spikes or recessed vertical pits. Because currently available methods are generally not capable of simultaneous 2D and 3D data acquisition, such methods may be significantly slower than either 2D or 3D data acquisition. In addition, 3D data acquisition may be significantly slower than 2D data acquisition thereby resulting in substantially reduced sampling for 3D in comparison to sampling for 2D. As used herein, the term "sampling" may generally refer to the number of points or locations inspected or measured on a single specimen during a process. In other words, if a relatively large percentage of a wafer may be scanned to acquire x-y data, then only a much smaller percentage of the wafer may be scanned to acquire additional z data.

There are several disadvantages to currently available systems and methods for three-dimensional inspection of bumped wafers. For example, as described above, such systems may be configured to scan a wafer more than once in series to acquire 2D and 3D data for inspection and metrology. In addition, configuration of such systems may be incompatible with rapid scanning of relatively large areas of bumped wafers. Such disadvantages will generally lower a throughput of an inspection and metrology system. Furthermore, such systems may be relatively complex due to the use of separate 2D and 3D data acquisition and processing systems. This disadvantage will generally increase cost and reduce reliability of an inspection and metrology system.

Therefore, improved systems and techniques for height measurement are needed.

BRIEF SUMMARY OF THE DISCLOSURE

In a first embodiment, an apparatus is provided. The apparatus includes a white light source that emits white light; a plurality of lenses; a pinhole aperture; a detector that receives the white light; a sensor body that includes a plurality of sensors; and a plurality of optical fibers connecting the white light source and the detector to the plurality of sensors. A refractive index of the lenses varies a focal distance of each wavelength of the white light from the white light source. Each of the wavelengths of the white light focuses at a different distance from the lenses. The sensors are disposed in the sensor body in a plurality of rows and columns. Each of the rows and the columns has at least two of the sensors.

A controller can be in electronic communication with the detector. The controller can be configured to provide height data about a wafer using a chromatic confocal technique.

An actuator can be configured to scan the sensor body and a wafer relative to each other. The wafer reflects the white light.

The sensors in rows and columns may be arranged in lines. The scan of the sensor body relative to the wafer can be in a direction non-parallel to any of the lines. In an instance, the direction of the scan of the sensor body relative to the wafer is at a 45° angle relative to at least one of the lines.

A chuck can be configured to hold a wafer that reflects the white light.

The detector can be a CMOS image sensor or a CCD image sensor with a spectral dispersion element. The spectral dispersion element may include a grating.

The pinhole aperture may be part of the optical fibers.

In a second embodiment, a method is provided. White light is directed at a wafer through a plurality of a lenses. A refractive index of the lenses varies a focal distance of each wavelength of the white light. Each of the wavelengths of the white light focuses at a different distance from the lenses. A portion of the white light reflected by the wafer is received at a plurality of sensors in a sensor body. The sensors are disposed in the sensor body in a plurality of rows and columns. Each of the rows and the columns has at least two of the sensors. Using a controller, height data about the wafer is determined using a chromatic confocal technique.

The method can further include scanning the wafer and the sensor body relative to each other.

The sensors in rows and columns can be in lines. The scanning of the sensor body relative to the wafer may be in a direction non-parallel to any of the lines. In an instance, the direction of the scanning of the sensor body relative to the wafer is at a 45° angle relative to at least one of the lines.

DESCRIPTION OF THE DRAWINGS

For a fuller understanding of the nature and objects of the disclosure, reference should be made to the following detailed description taken in conjunction with the accompanying drawings, in which.

DETAILED DESCRIPTION OF THE DISCLOSURE

Although claimed subject matter will be described in terms of certain embodiments, other embodiments, including embodiments that do not provide all of the benefits and features set forth herein, are also within the scope of this disclosure. Various structural, logical, process step, and electronic changes may be made without departing from the scope of the disclosure. Accordingly, the scope of the disclosure is defined only by reference to the appended claims.

Embodiments disclosed herein can be used for height measurements, such as those for bumps, pillars, or film thickness. Measuring speed is increased by using chromatic confocal techniques with embodiments of the sensor arrangement, which improves throughput.

A chromatic confocal technique can use a white light source, such as an LED, that passes through multiple lenses. The white light source can illuminate a surface of a wafer. The lenses can have a high degree of chromatic aberration. A refractive index of the lenses can vary a focal distance of each wavelength of the white light from the white light source. Thus, each wavelength of the white light will focus at a different distance from the lenses, which creates a measurement range. The light can travel via one or more fibers to sensors of an optical probe which then spreads the focal length over a discrete number of points creating a full spectrum of light.

When a surface of interest is within the measurement range, a single wavelength of the white light will be in focus while all others will be out of focus. The white light is then reflected back through the lenses, then through a pinhole aperture that allows only the focused wavelength to pass through to a CCD spectrometer, which will indicate the wavelength in focus corresponding to a specific distance for a single point.

Figure 1:
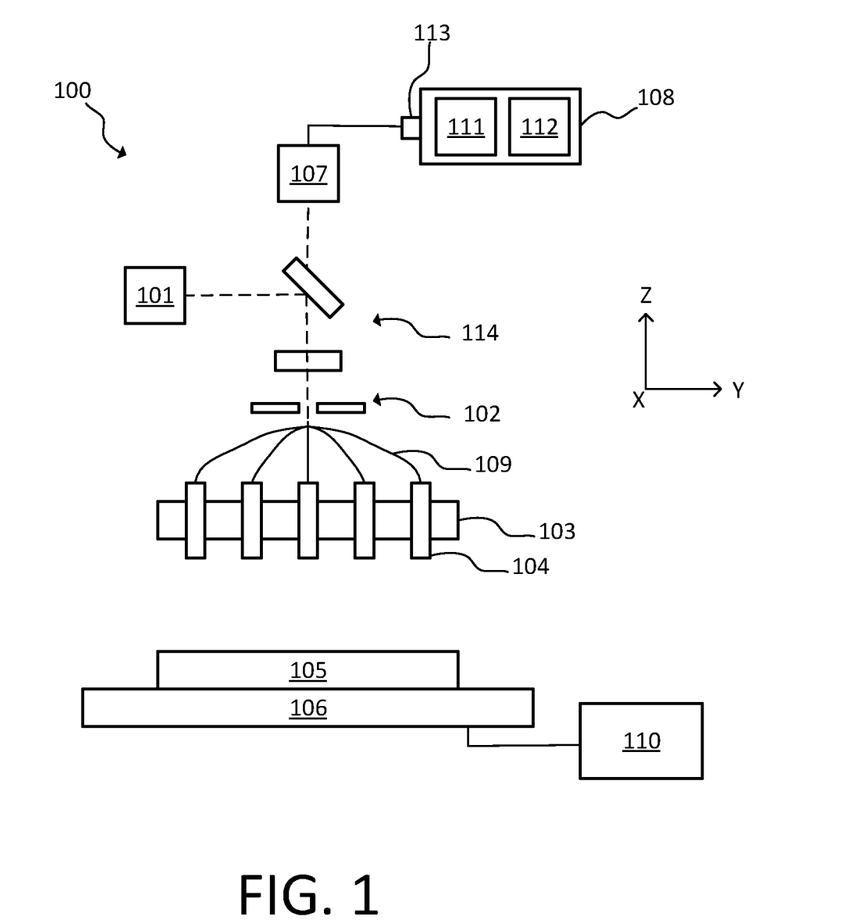
FIG. 1 is a cross-sectional block diagram of an embodiment in accordance with the present disclosure.

FIG. 1 is a cross-sectional block diagram of an apparatus 100. The apparatus 100 can be used for chromatic confocal height measurement of features or surfaces of a wafer 105.

The apparatus 100 includes a white light source 101 that emits white light and a plurality of lenses 114. For example, the lenses 114 can include a beam splitter and other lenses. A refractive index of the lenses 114 varies a focal distance of each wavelength of the white light from the white light source 101. Each of the wavelengths of the white light focuses at a different distance from the lenses 114.

For example, the white light source 101 may be configured for bright field confocal imaging or dark field confocal imaging. One or more white light sources 101 can be configured to emit relatively short wavelength light. Therefore, the white light source 101 may have a relatively short depth of focus. For example, a confocal illumination system may be configured to illuminate a wafer 105 with a single point or a line. In addition, a confocal illumination system may be configured to illuminate multiple locations on a wafer 105 with multiple points or multiple lines substantially simultaneously.

A white light source 101 may be configured to generate a beam of white light. In addition, the white light source 101 may be configured to generate a beam of white light having more than one wavelength. For example, a white light source 101 may include a laser configured to emit multiple wavelengths of light. The laser may include an argon ion laser configured to emit light having wavelengths including about 455 nm, about 458 nm, about 466 nm, about 477 nm, about 488 nm, about 497 nm, about 502 nm, about 515 nm, or about 529 nm. An argon ion laser may also be configured to emit light having wavelengths in the ultraviolet and infrared ranges. The white light source 101 may include other light sources such as a light source configured to emit broadband light. For example, the white light source 101 may be configured to a beam of broadband light that may include ultraviolet light, visible light, and/or infra-red light. A suitable broadband white light source 101 may include, but is not limited to, a mixed gas laser configured to generate light in a range of wavelengths from about 450 nm to about 647 nm. Furthermore, the system may include multiple light sources. For example, the system may include two lasers.

The two lasers may be configured to generate beams of light having substantially different wavelengths.

The lenses 114 can include a light intensity attenuator, a spectral line bandpass filter, a polarizing beam splitter, a spatial filter, focusing optics, a collimator lens, a scan lens, a field lens, a tube lens, a quarter wave plate, a bright field cube, or folding mirrors.

The apparatus 100 also may include one or more filters (not shown) coupled to the white light source 101. The filters may be configured to transmit a number of wavelengths of the light emitted by the white light source 101. For example, the filters may be configured to transmit two or three or more wavelengths of the light. Light transmitted by the filters may be directed to a surface of a wafer 105 such that multiple wavelengths of light may be incident upon wafer 105.

The white light source 101 may be parallelized using the lenses 114.

The apparatus 100 also includes a pinhole aperture 102.

A sensor body 103 includes a plurality of sensors 104. The sensors 104 are disposed in the sensor body 103 in a plurality of rows and columns. Each of the rows and the columns has at least two of the sensors 104. While five sensors 104 are illustrated in one row, there may be, for example, hundreds of sensors 104 per sensor body 103 in multiple rows and columns.

One or more optical fibers 109 connect the white light source 101 and the detector 107 to the plurality of sensors 104. The white light projected onto the wafer 105 through the sensors 104 may be in the form of a slot or a line. While illustrated as separate from the pinhole aperture 102 in FIG. 1, the optical fibers 109 can serve as or can include a pinhole aperture 102. Thus, the pinhole aperture 102 may be part of the optical fibers 109. For example, the pinhole aperture 102 may be one or more faces of the optical fibers 109.

A detector 107 receives the white light reflected from the wafer 105. The detector 107 may be, for example, a CMOS image sensor or a CCD image sensor with a spectral dispersion element, such as a grating.

A controller 108 is in electronic communication with the detector 107. The controller 108 is configured to provide height data about the wafer 105 using a chromatic confocal technique.

The controller 108 can include one or more processors 408 and one or more memory 112. Each processor 111 may be in electronic communication with one or more of the memory 112. In an embodiment, the one or more processors 408 are communicatively coupled. In this regard, the one or more processors 408 may receive readings related to the wavelengths received at the detector 107 and store the reading in the memory 112 of the controller 108. The controller 108 also may include a communication port 113 in electronic communication with at least one processor 111. The controller 108 may be part of the system itself or may be separate from the system (e.g., a standalone control unit or in a centralized quality control unit).

It is to be appreciated that the controller 108 may be implemented in practice by any combination of hardware, software, and firmware. Also, its functions as described herein may be performed by one unit, or divided up among different components, each of which may be implemented in turn by any combination of hardware, software, and firmware. Program code or instructions for the controller 108 to implement various methods and functions may be stored in controller readable storage media, such as a memory 112, within the controller 108, external to the controller 108, or combinations thereof.

The controller 108, other system(s), or other subsystem(s) described herein may take various forms, including a personal computer system, workstation, image computer, mainframe computer system, workstation, network appliance, internet appliance, parallel processor, or other device. In general, the term "control unit" may be broadly defined to encompass any device having one or more processors that executes instructions from a memory medium. The subsystem(s) or system(s) may also include any suitable processor known in the art, such as a parallel processor. In addition, the subsystem(s) or system(s) may include a platform with high speed processing and software, either as a standalone or a networked tool.

If the system includes more than one subsystem, then the different subsystems may be coupled to each other such that images, data, information, instructions, etc. can be sent between the subsystems. For example, one subsystem may be coupled to additional subsystem(s) by any suitable transmission media, which may include any suitable wired and/or wireless transmission media known in the art. Two or more of such subsystems may also be effectively coupled by a shared computer-readable storage medium (not shown).

In another embodiment, the controller 108 may be communicatively coupled to any of the various components or sub-systems of system 100 in any manner known in the art. Moreover, the controller 108 may be configured to receive and/or acquire data or information from other systems (e.g., inspection results from an inspection system such as a broad band plasma (BBP) tool, a remote database including design data and the like) by a transmission medium that may include wired and/or wireless portions. In this manner, the transmission medium may serve as a data link between the controller 108 and other subsystems of the system 100 or systems external to system 100.

The controller 108 may be coupled to the components of the system 100 in any suitable manner (e.g., via one or more transmission media, which may include wired and/or wireless transmission media) such that the controller 108 can receive the output generated by the system 100. The controller 108 may be configured to perform a number of functions using the output. In another example, the controller 108 may be configured to send the output to a memory 112 or another storage medium without performing defect review on the output. The controller 108 may be further configured as described herein.

An additional embodiment relates to a non-transitory computer-readable medium storing program instructions executable on a controller for performing a computer-implemented method for determining heights of features on a wafer 105, as disclosed herein. In particular, as shown in FIG. 1, the controller 108 can include a memory 112 or other electronic data storage medium with non-transitory computer-readable medium that includes program instructions executable on the controller 108. The computer-implemented method may include any step(s) of any method(s) described herein. The memory 112 or other electronic data storage medium may be a storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes (MFC), SSE (Streaming SIMD Extension), or other technologies or methodologies, as desired.

In some embodiments, various steps, functions, and/or operations of system 400 and the methods disclosed herein are carried out by one or more of the following: electronic circuits, logic gates, multiplexers, programmable logic devices, ASICs, analog or digital controls/switches, microcontrollers, or computing systems. Program instructions implementing methods such as those described herein may be transmitted over or stored on carrier medium. The carrier medium may include a storage medium such as a read-only memory, a random access memory, a magnetic or optical disk, a non-volatile memory, a solid state memory, a magnetic tape and the like. A carrier medium may include a transmission medium such as a wire, cable, or wireless transmission link. For instance, the various steps described throughout the present disclosure may be carried out by a single controller 108 (or computer system) or, alternatively, multiple controllers 108 (or multiple computer systems). Moreover, different sub-systems of the system 100 may include one or more computing or logic systems. Therefore, the above description should not be interpreted as a limitation on the present invention but merely an illustration.

In the system 100, the wafer 105 can be held by a chuck 106. An actuator 110 can be configured to scan the sensor body 103 and a wafer 105 relative to each other. For example, the chuck 106 with the wafer 105 can be scanned relative to the sensor body 103 in the X or Y directions. While the actuator 110 is illustrated as moving the chuck 106, the actuator 110 also can move the sensor body 103.

Figure 2:
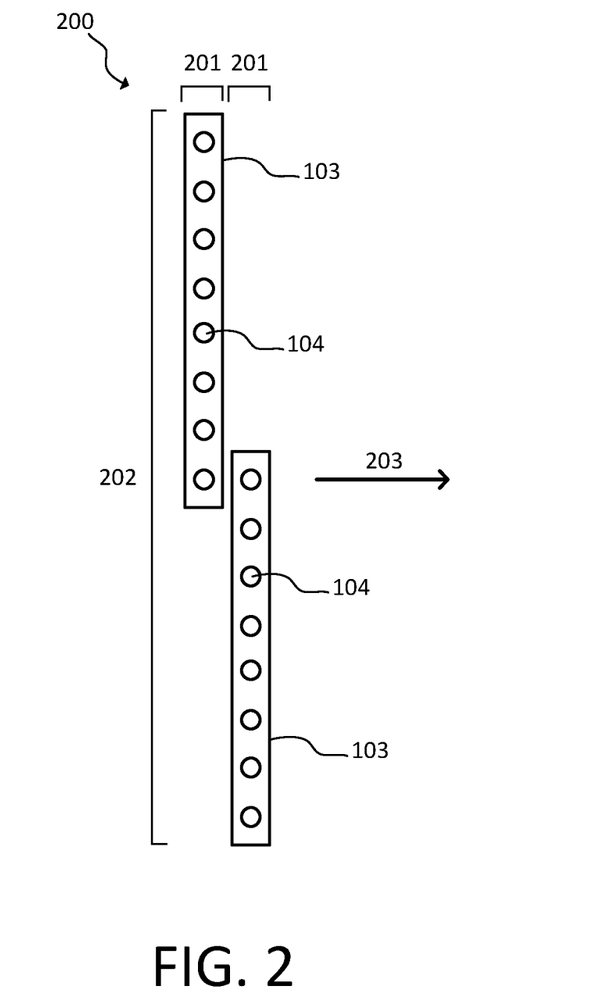
FIGS. 2-4 illustrate embodiments of sensor arrangements in accordance with the present disclosure.
Figure 3:
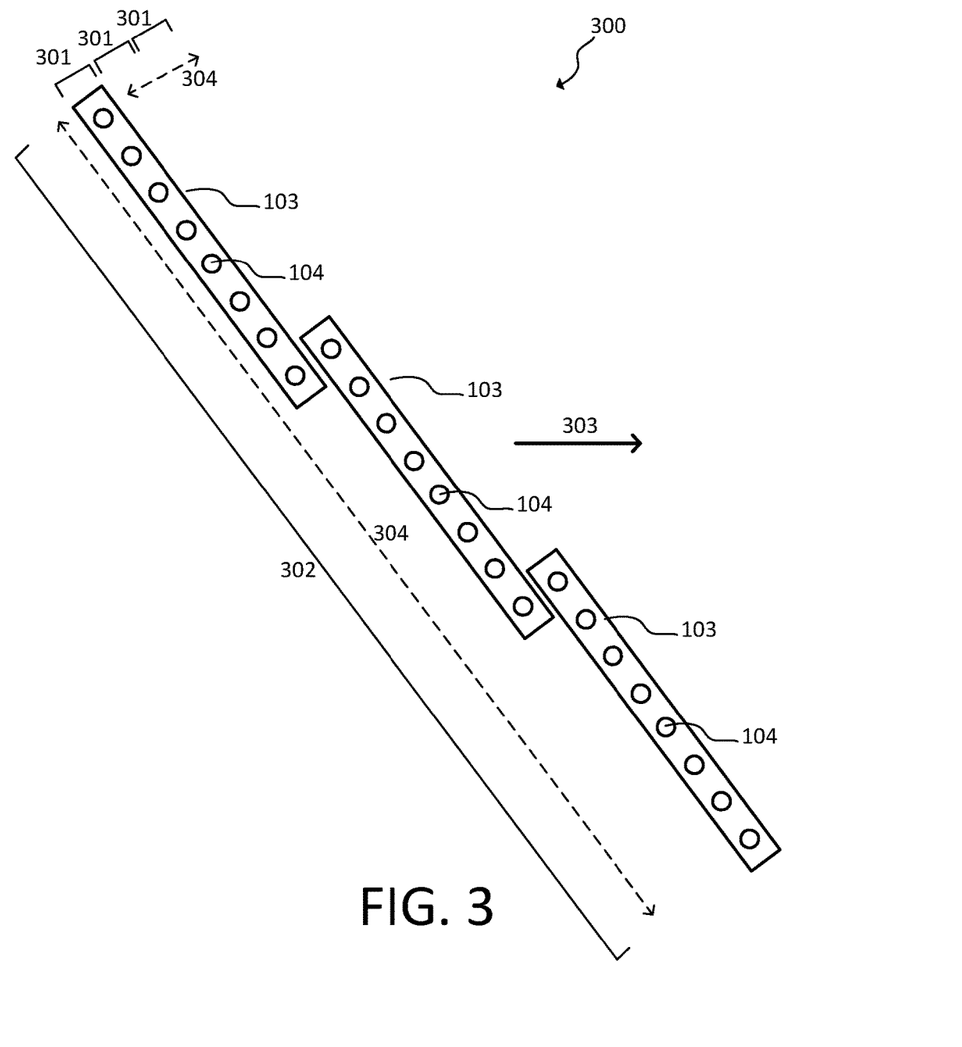
Figure 4:
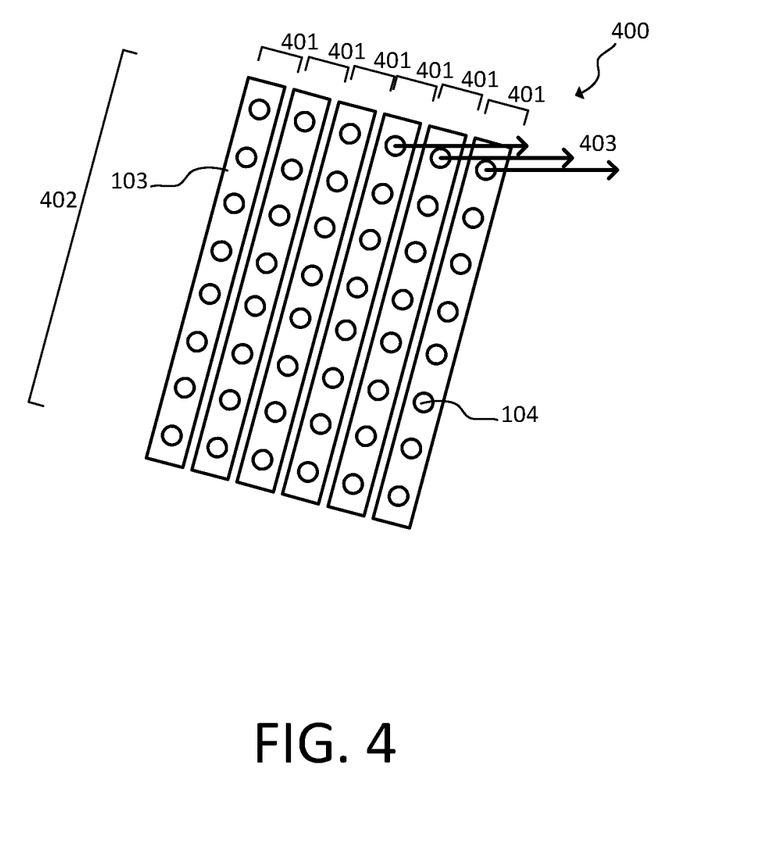

FIGS. 2-4 illustrate embodiments of sensor arrangements. While eight sensors are illustrated in each sensor body in FIGS. 2-4, there may be, for example, hundreds of sensors per sensor body.

In FIG. 2, the arrangement 200 includes two sensor bodies 103. These sensor bodies 103 are arranged in two rows 201. Each row 201 and column 202 includes at least two sensors 104. The two sensor bodies 103 can at least partially overlap. A wafer (not illustrated) moves relative to the sensor bodies 103 as shown with the arrow 203.

In FIG. 3, the arrangement 300 includes three sensor bodies 103. These sensor bodies 103 are arranged in three rows 301. Each row 301 and column 302 includes at least two sensors 104. The three sensor bodies 103 can at least partially overlap. A wafer (not illustrated) moves relative to the sensor bodies 103 as shown with the arrow 303. The sensors 104 in the rows 301 and columns 302 are arranged in lines 304 (shown with dotted lines). The scan of a sensor body 103 relative to the wafer is in a direction non-parallel to any of the lines 304, as seen comparing the arrow 303 with the lines 304. In an instance, the direction of the scan of a sensor body 103 relative to the wafer is at a 45° angle relative to at least one of the lines 304.

In FIG. 4, the arrangement 400 includes six sensor bodies 103. These sensor bodies 103 are arranged in six rows 401. Each row 401 and column 402 includes at least two sensors 104. The six sensor bodies 103 can at least partially overlap. For example, the six sensor bodies 103 can be arranged to fully overlap with each other. A wafer (not illustrated) moves relative to the sensor bodies 103 as shown with the arrow 403.

Figure 5:
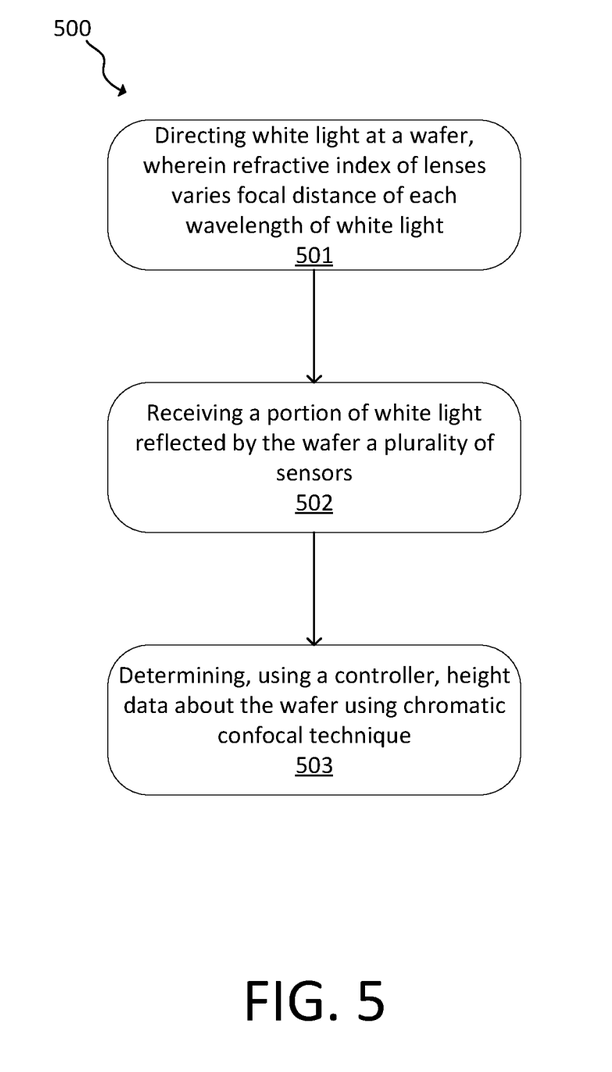
FIG. 5 is a flowchart of an embodiment in accordance with the present disclosure.

FIG. 5 is a flowchart of a method 500. At 501, white light is directed at a wafer. The refractive index of the lenses varies a focal distance of each wavelength of the white light. Each of the wavelengths of the white light focuses at a different distance from the lenses.

At 502, a portion of the white light reflected by the wafer is received at a plurality of sensors in a sensor body. The sensors are disposed in the sensor body in a plurality of rows and columns. Each of the rows and the columns has at least two of the sensors.

Using a controller, height data about the wafer is determined at 503 using a chromatic confocal technique.

The wafer and the sensor body may be scanned relative to each other. For example, a byzantine scan pattern may be used. In an instance, the rows and the columns are in lines and the scanning of the sensor body relative to the wafer may in a direction non-parallel to any of the lines. For example, the direction of the scanning of the sensor body relative to the wafer can be at 45° angle relative to at least one of the lines.

A brighter light source also can provide enhanced speed for chromatic confocal imaging. Throughput may be limited by the sensor output. Laser-driven plasma sources or supercontinuum sources are examples of brighter light sources that can provide enhanced speed for chromatic confocal imaging.

As used herein, the term "wafer" generally refers to substrates formed of a semiconductor or non-semiconductor material. Examples of such a semiconductor or non-semiconductor material include, but are not limited to, monocrystalline silicon, gallium nitride, gallium arsenide, indium phosphide, sapphire, and glass. Such substrates may be commonly found and/or processed in semiconductor fabrication facilities.

A wafer may include one or more layers formed upon a substrate. For example, such layers may include, but are not limited to, a photoresist, a dielectric material, a conductive material, and a semiconductive material. Many different types of such layers are known in the art, and the term wafer as used herein is intended to encompass a wafer including all types of such layers.

One or more layers formed on a wafer may be patterned or unpatterned. For example, a wafer may include a plurality of dies, each having repeatable patterned features or periodic structures. Formation and processing of such layers of material may ultimately result in completed devices. Many different types of devices may be formed on a wafer, and the term wafer as used herein is intended to encompass a wafer on which any type of device known in the art is being fabricated.

Other types of wafers also may be used. For example, the wafer may be used to manufacture LEDs, solar cells, magnetic discs, flat panels, or polished plates. Defects on other objects also may be classified using techniques and systems disclosed herein.

Each of the steps of the method may be performed as described herein. The methods also may include any other step(s) that can be performed by the controller and/or computer subsystem(s) or system(s) described herein. The steps can be performed by one or more computer systems, which may be configured according to any of the embodiments described herein. In addition, the methods described above may be performed by any of the system embodiments described herein.

Although the present disclosure has been described with respect to one or more particular embodiments, it will be understood that other embodiments of the present disclosure may be made without departing from the scope of the present disclosure. Hence, the present disclosure is deemed limited only by the appended claims and the reasonable interpretation thereof.

What is claimed is:

1. An apparatus comprising:
 a white light source that emits white light;
 a plurality of lenses including a beam splitter and a refractive lens, wherein a refractive index of the plurality of lenses varies a focal distance of each wavelength of the white light from the white light source, wherein each of the wavelengths of the white light focuses at a different distance from the plurality of lenses, and wherein the beam splitter is configured to direct the white light from the white light source to the refractive lens;
 a pinhole aperture, wherein the refractive lens is disposed along a path of the white light between the beam splitter and the pinhole aperture;
 a detector that receives the white light from the beam splitter;
 a sensor body that includes a plurality of sensors, wherein the sensors are disposed in the sensor body in a plurality of rows and columns, each of the rows and the columns having at least two of the sensors; and
 a plurality of optical fibers connecting the white light source and the detector to the plurality of sensors, wherein the optical fibers are disposed between the sensors and the pinhole aperture along the path of the white light.

2. The apparatus of claim 1, further comprising a controller in electronic communication with the detector, wherein the controller is configured to provide height data about a wafer using a chromatic confocal technique.

3. The apparatus of claim 1, further comprising an actuator configured to scan the sensor body and a wafer that reflects the white light relative to each other.

4. The apparatus of claim 3, wherein the sensors in rows and the columns are arranged in lines, and wherein the scan of the sensor body relative to the wafer is in a direction non-parallel to any of the lines.

5. The apparatus of claim 4, wherein the direction of the scan of the sensor body relative to the wafer is at a 45° angle relative to at least one of the lines.

6. The apparatus of claim 1, further comprising a chuck configured to hold a wafer that reflects the white light.

7. The apparatus of claim 1, wherein the detector is a CMOS image sensor or a CCD image sensor with a spectral dispersion element.

8. The apparatus of claim 7, wherein the spectral dispersion element includes a grating.

9. The apparatus of claim 1, wherein the pinhole aperture is part of the optical fibers.

10. A method comprising:
 directing white light at a wafer through a plurality of lenses that include a beam splitter and a refractive lens, wherein a refractive index of the plurality of lenses varies a focal distance of each wavelength of the white light, and wherein each of the wavelengths of the white light focuses at a different distance from the plurality of lenses;
 receiving a portion of the white light reflected by the wafer at a plurality of sensors in a sensor body, wherein the sensors are disposed in the sensor body in a plurality of rows and columns, each of the rows and the columns having at least two of the sensors;
 transmitting the portion of the white light received at the plurality of sensors through a plurality of optical fibers;
 projecting the portion of the white light from the plurality of optical fibers to a pinhole aperture;
 projecting the portion of the white light from the pinhole aperture to the refractive lens;
 projecting the portion of the white light from the refractive lens to the beam splitter;
 projecting the portion of white light from the beam splitter to a detector; and
 determining, using the detector and a controller, height data about the wafer using a chromatic confocal technique.

11. The method of claim 10, further comprising scanning the wafer and the sensor body relative to each other.

12. The method of claim 11, wherein the sensors in the rows and the columns are in lines, and wherein the scanning of the sensor body relative to the wafer is in a direction non-parallel to any of the lines.

13. The method of claim 12, wherein the direction of the scanning of the sensor body relative to the wafer is at a 45° angle relative to at least one of the lines.

* * * * *